US006472569B1

(12) United States Patent
Wu et al.

(10) Patent No.: US 6,472,569 B1
(45) Date of Patent: Oct. 29, 2002

(54) SILICOALUMINOPHOSPHATE MATERIAL, A METHOD OF MAKING SUCH IMPROVED MATERIAL AND THE USE THEREOF IN THE CONVERSION OF OXYGENATED HYDROCARBONS TO AN OLEFIN AND/OR AN ETHER

(75) Inventors: An-hsiang Wu; Jianhua Yao, both of Bartlesville; Charles A. Drake, Nowata, all of OK (US)

(73) Assignee: Phillips Petroleum Company, Bartlesville, OK (US)

( * ) Notice: Subject to any disclaimer, the term of this patent is extended or adjusted under 35 U.S.C. 154(b) by 0 days.

(21) Appl. No.: 09/292,866

(22) Filed: Apr. 16, 1999

(51) Int. Cl.$^7$ .............................. C07C 41/09; C07C 1/00; B01J 21/12
(52) U.S. Cl. ....................... 568/698; 568/671; 585/638; 585/639; 585/640; 502/202; 502/208; 502/214; 502/232; 502/240; 502/263
(58) Field of Search ................................. 568/671, 698; 585/638, 639, 640; 502/202, 208, 214, 232, 240, 263

(56) References Cited

U.S. PATENT DOCUMENTS

| 4,499,327 A | * | 2/1985 | Kaiser ..................... 585/640 |
|---|---|---|---|
| 4,849,575 A | | 7/1989 | Lewis ..................... 585/640 |
| 4,873,390 A | | 10/1989 | Lewis et al. ............... 585/638 |
| 4,960,954 A | | 10/1990 | Hoelderich et al. ......... 568/691 |
| 5,013,535 A | * | 5/1991 | Bedard et al. ............. 423/277 |
| 5,130,435 A | * | 7/1992 | Hoelderich et al. ......... 546/256 |
| 5,233,117 A | | 8/1993 | Barger .................... 585/640 |
| 5,248,647 A | | 9/1993 | Barger .................... 502/214 |
| 5,475,182 A | | 12/1995 | Janssen ................... 585/640 |
| 6,046,371 A | | 4/2000 | Wu et al. .................. 585/638 |
| 6,051,745 A | | 4/2000 | Wu et al. .................. 585/638 |

* cited by examiner

*Primary Examiner*—Rosalynd Keys
(74) *Attorney, Agent, or Firm*—Charles W. Stewart

(57) ABSTRACT

A catalyst system comprising a silicoaluminophosphate impregnated with a compound selected from the group consisting of phosphoric acid, boric acid, tributyltin acetate, and combinations of any two or more thereof, and a method of preparing such catalyst system, are disclosed. The thus-obtained catalyst system is employed as a catalyst in the conversion of a hydrocarbon feedstock comprising oxygenated hydrocarbons to olefins and/or ethers.

27 Claims, No Drawings

SILICOALUMINOPHOSPHATE MATERIAL, A METHOD OF MAKING SUCH IMPROVED MATERIAL AND THE USE THEREOF IN THE CONVERSION OF OXYGENATED HYDROCARBONS TO AN OLEFIN AND/OR AN ETHER

BACKGROUND OF THE INVENTION

The invention relates to catalyst systems useful in hydrocarbon upgrading processes and to methods for their production and use. In another aspect, this invention relates to processes for converting oxygenated hydrocarbons to $C_2$–$C_4$ olefins and/or ethers, such as dimethyl ether (DME), with an increase in olefin or ether selectivity and a reduction in coke formation resulting from the conversion of such oxygenated hydrocarbons in the presence of such catalyst systems. The term "oxygenated hydrocarbons" as employed herein comprises hydrocarbons containing aliphatic moieties such as, but not limited to, alcohols, halides, mercaptans, sulfides, amines, ethers, and carbonyl compounds (aldehydes, ketones, carboxylic acids and the like) or mixtures thereof.

It is known to convert oxygenated hydrocarbons to olefins and/or ethers in the presence of catalysts which contain a silicoaluminophosphate (SAPO), as is described in U.S. Pat. Nos. 4,861,938; 5,475,182; 5,248,647 and 5,663,471, the disclosures of each are incorporated herein by reference.

One concern with the use of SAPO catalysts in the conversion of oxygenated hydrocarbons to olefins and/or ethers is the excessive production of coke during the conversion reaction. Coke formed during the SAPO catalyzed conversion of oxygenated hydrocarbons tends to cause catalyst deactivation. It is desirable to improve processes for the conversion of oxygenated hydrocarbons to olefins and/or ethers by minimizing the amount of coke formed during such processes. It is also desirable to have a SAPO catalyst that is useful in producing significant quantities of olefin and/or ether conversion products.

SUMMARY OF THE INVENTION

It is an object of this invention to provide an improved SAPO material which when used in the conversion of oxygenated hydrocarbons results in increased olefin yield and decreased coke production.

A further object of this invention is to provide a method for making an improved SAPO material having such desirable properties as providing for increased olefin yield and decreased coke production when used in the conversion of oxygenated hydrocarbons.

Another object of this invention is to provide an improved process for the conversion of oxygenated hydrocarbons in which the yield of olefins is increased and the production of coke is decreased.

Yet another object of this invention is to provide an improved SAPO material which when used in the conversion of oxygenated hydrocarbons results in increased ether yield and decreased coke production.

A yet further object of this invention is to provide a method for making an improved SAPO material having such desirable properties as providing for increased ether yield and decreased coke production when used in the conversion of oxygenated hydrocarbons.

Yet another object of this invention is to provide an improved process for the conversion of oxygenated hydrocarbons in which the yield of ether is increased and the production of coke is decreased.

The inventive catalyst system comprises a SAPO impregnated with a compound selected from the group consisting of phosphoric acid, boric acid, tributyltin acetate, and combinations of any two or more thereof. The inventive catalyst system can be prepared by impregnating the SAPO, under suitable conditions, with such compound. The inventive catalyst system can be used in the conversion of an oxygenated hydrocarbon to olefins and/or ethers by contacting, under conversion conditions, a hydrocarbon feedstock with the inventive catalyst system.

Other objects and advantages of the invention will become apparent from the detailed description and the appended claims.

DETAILED DESCRIPTION OF THE INVENTION

The SAPO material used in preparing the inventive catalyst system can be any SAPO that is effective in the conversion of oxygenated hydrocarbons to olefins and/or ethers when contacted under conversion conditions with oxygenated hydrocarbons.

SAPO catalysts exhibit properties of both aluminosilicate zeolites and aluminophosphates. The SAPO's have a three-dimensional microporous crystal framework structure of $PO_2$, $AlO_2$ and $SiO_2$ tetrahedral units. The chemical composition (anhydrous) is:

$$mR:(Si_xAl_yP_z)O_2$$

wherein "R" represents at least one organic templating agent present in the intracrystalline pore system; "m" represents the moles of "R" present per mole of $(Si_xAl_yP_z)O_2$ and has a value of from zero to 0.3, the maximum value in each case depending upon the molecular dimensions of the templating agent and the available void volume of the pore system of the particular SAPO species involved, and "x", "y" and "z" represent the mole fractions of silicon, aluminum and phosphorus, respectively.

Examples of such templating agents include, but are not limited to, tetramethylammonium hydroxide, tetraethylammonium hydroxide, and tetrapropylammonium hydroxide. Further details relating to the formation of SAPO compositions, including molar amounts of each oxide source, can be found in the Lok et al. U.S. Pat. No. 4,440,871, the entire disclosure of which is expressly incorporated herein by reference.

SAPO compositions useful in the present invention include, but are not limited to, SAPO-4, SAPO-5, SAPO-11, SAPO-16, SAPO-17, SAPO-20, SAPO-31, SAPO-34, SAPO-35, SAPO-37, SAPO-40, SAPO-41, SAPO-42, and SAPO-44. The presently more preferred SAPO is SAPO-34.

The SAPO can be combined or mixed with a binder material in a liquid such as water or a hydrocarbon, by any means known to one skilled in the art such as stirring, blending, kneading, or extrusion, following which the resulting mixture can be dried in air at a temperature in the range of from about 20° C. to about 125° C., for a time period in the range of from about 0.5 hour to about 4 hours under any pressures that accommodate the temperatures, preferably atmospheric pressure.

Any binders known to one skilled in the art for use with a SAPO are suitable for use herein. Examples of suitable binders include, but are not limited to, aluminas such as for example α-alumina and γ-alumina; silicas; alumina-silica; aluminum phosphate; aluminum chlorohydrate; clays such as kaolinite, halloysite, vermiculite, chlorite, attapulgite, smectite, montmorillonite, illite, saconite, sepiolite, palygorskite, and combinations of any two or more thereof. Because these binders are well known to one skilled in the art, descriptions of which are omitted herein. The presently preferred binder, if employed, is silica.

The SAPO, or SAPO-binder mixture, can be extruded into pellets or tablets by any method known to those skilled in the art.

The SAPO, whether bound in a SAPO-binder mixture, and whether or not extruded, can be impregnated with a compound selected from the group consisting of phosphoric acid, boric acid, tributyltin acetate, and combinations of any two or more thereof, by any suitable means or method known in the art for impregnating such compounds into a substrate material to thereby form an impregnated SAPO.

It is preferred to use any standard incipient wetness technique for impregnating the SAPO with such compound. A preferred method uses a liquid impregnation solution containing the desirable concentration of the compound. The concentration of the compound in the impregnation solution is generally in the range of from about 0.01 to about 10 mole percent, preferably from about 0.05 to about 7 mole percent, and most preferably from 0.1 to 5 mole percent, based on the total moles of the solution.

When the compound is phosphoric acid or boric acid it is particularly desirable to use an aqueous solution formed by dissolving the compound in water. When the compound is tributyltin acetate it is particularly desirable to use a solution formed by dissolving the tributyltin acetate in a hydrocarbon solvent, such as in a $C_6$ to $C_{10}$ cycloalkane, benzene, toluene, ethylbenzene, xylene(s), and the like. The presently preferred solvent for tributyltin acetate is cyclohexane.

The weight percent of the compound present in the impregnated SAPO is generally in the range upwardly to about 20 weight percent, preferably from about 0.01 to about 15 weight percent, and most preferably from 0.1 to 10 weight percent, based on the total weight of the impregnated SAPO.

The impregnated SAPO, whether impregnated with phosphoric acid, boric acid or tributyltin acetate, can be calcined by any suitable means or method known in the art whereby it is exposed to an atmosphere of inert gas, air or combinations thereof, under temperature and pressure conditions and for a period of time that suitably provide a calcined impregnated SAPO such that at least a portion of the metal present in the compound impregnated into the SAPO is converted to a metal oxide form.

The calcination temperature is generally in the range of from about 200° C. to about 1000° C., preferably from about 300° C. to about 750° C., and most preferably from 350° C. to 650° C., the calcination pressure is generally in the range of from about 0 to about 50 atmospheres (atm), preferably from about 0.1 to about 30 atm, and most preferably from 0.5 to 10 atm. The calcination can be performed in either an air atmosphere or an inert atmosphere or a combination thereof for a time period in the range of from about 0.1 hour to about 30 hours, preferably from about 2 hours to about 20 hours, and most preferably from 3 hours to 15 hours.

Any suitable hydrocarbon feedstock, which comprises oxygenated hydrocarbons, can be used as the feed to be contacted with the inventive catalyst system under suitable process conditions for obtaining a reaction product comprising olefins and/or ethers. The aliphatic moieties of the oxygenated hydrocarbons preferably contain in the range of from about 1 to about 10 carbon atoms, and more preferably, contain from about 1 to about 4 carbon atoms. Representative oxygenated hydrocarbons include, but are not limited to, lower straight or branched chain alcohols, their unsaturated counterparts and the nitrogen, halogen and sulfur analogues of such. Examples of suitable compounds include, but are not limited to, methanol, isopropanol; n-propanol; ethanol; fuel alcohols; methyl mercaptan, methyl sulfide; methyl amine, dimethyl ether (for olefin production); ethyl mercaptan; ethyl chloride; diethyl ether; methylethyl ether; formaldehyde; dimethyl ketone; acetic acid; n-alkyl amines; n-alkyl halides and n-alkyl sulfides wherein the n-alkyl groups contain 3 to 10 carbon atoms; and mixtures of any two or more thereof. The presently preferred oxygenated hydrocarbon is methanol.

The hydrocarbon feedstock can be contacted, by any suitable manner, with the inventive catalyst system described herein contained within a reaction zone which will provide the desired decrease in coke production and/or the desired conversion to olefins and/or ethers. The contacting step can be operated as a batch process step or, preferably, as a continuous process step. In the latter operation, a solid catalyst bed or a moving catalyst bed or a fluidized catalyst bed can be employed. Any of these operational modes have advantages and disadvantages, and those skilled in the art can select the one most suitable for a particular feed and catalyst.

The contacting step is preferably carried out within a conversion reaction zone, wherein is contained the inventive catalyst system, and under reaction conditions that suitably promote the formation of olefins and/or ethers from at least a portion of the oxygenated hydrocarbons of the hydrocarbon feedstock. The reaction temperature of the contacting step is generally in the range of from about 200° C. to about 800° C., preferably from about 250° C. to about 750° C. and, most preferably, from 300° C. to 700° C. The contacting pressure can generally range from about 0 psig to about 500 psig, preferably, from about atmospheric pressure to about 450 psig and, most preferably, from atmospheric pressure to 400 psig.

The flow rate at which the hydrocarbon feedstock is charged to the conversion reaction zone is such as to provide a weight hourly space velocity ("WHSV") in the range of from about 0.01 hour$^{-1}$ upwardly to about 1000 hours$^{-1}$. The term "weight hourly space velocity", as used herein, shall mean the numerical ratio of the rate at which a hydrocarbon feedstock is charged to the conversion reaction zone in pounds per hour divided by the pounds of catalyst contained in the conversion reaction zone to which the hydrocarbon is charged. The preferred WHSV of the feed to the conversion reaction zone or contacting zone can be in the range of from about 0.25 hour$^{-1}$ to about 250 hours$^{-1}$ and, most preferably, from 0.5 hour$^{-1}$ to 100 hours$^{-1}$.

The process is generally carried out in the presence of one or more inert diluents which can be present in an amount in the range of from about 1 to about 99 molar percent, based on the total number of moles of all feed and diluent components fed to the reaction zone. Suitable diluents include, but are not limited to, helium, argon, nitrogen, carbon monoxide, carbon dioxide, hydrogen, water, paraffins, hydrocarbons (such as methane and the like), aromatic compounds, and mixtures of any two or more thereof. The presently preferred diluent is water.

As a further embodiment of the present invention, when the compound is phosphorous, it has been unexpectedly found that contacting the hydrocarbon feedstock with the inventive catalyst system preferentially produces either olefins or ethers, depending on the concentration of phosphoric acid in the impregnating solution (described above).

The reaction product produced from contacting the hydrocarbon feedstock with the inventive catalyst system preferentially comprises at least one olefin when the SAPO impregnation, as described above, includes a solution comprising phosphoric acid present in the solution in the range of from about 0.5 to less than about 10 weight percent (about 0.1 to less than about 2.2 mole percent), preferably from about 0.8 to about 7 weight percent (about 0.2 to about 1.5 mole percent), and most preferably from 1 to 5 weight percent (0.2 to 1.1 mole percent), based on the total weight or moles of the solution, respectively.

The impregnated SAPO can be calcined, as described above, prior to contact with the hydrocarbon feedstock.

The reaction product produced from contacting the hydrocarbon feedstock with the inventive catalyst system preferentially comprises at least one ether, preferably DME, when the SAPO impregnation, as described above, includes a solution comprising phosphoric acid present in the solution in the range of from about 10 to about 40 weight percent (about 2.2 to about 8.8 mole percent), preferably from about 12 to about 35 weight percent (about 2.6 to about 7.7 mole percent), and most preferably from 15 to 30 weight percent (3.3 to 6.6 mole percent), based on the total weight or moles of the solution, respectively.

The impregnated SAPO can be calcined, as described above, prior to contact with the hydrocarbon feedstock.

The following examples are presented to further illustrate this invention and are not to be construed as unduly limiting its scope.

EXAMPLE 1

This example illustrates the preparation of catalysts which were subsequently tested as catalysts in the conversion of a hydrocarbon feedstock comprising methanol to olefins and/or DME.

Catalyst A (Control)

A 50 gram quantity of a commercially available SAPO-34 catalyst (provided by UOP, LLC, Des Plaines, Ill. under product designation SAPO-34) was mixed with a 100 gram quantity of a colloidal silica solution (manufactured by DuPont under product designation Ludox® AS-40). The formed mixture was then extruded into 1/16" diameter pellets and dried at room temperature followed by calcining at a temperature of about 538° C. for 6 hours.

Catalyst B (Invention)

A 2 gram quantity of Catalyst A was impregnated, by incipient wetness, with an aqueous solution containing 5 weight percent (1.7 mole percent) boric acid. The thus obtained impregnated material was calcined at a temperature of about 538° C. for 6 hours.

Catalyst C (Invention)

A 2 gram quantity of Catalyst A was impregnated, by incipient wetness, with a solution containing 3.6 weight percent (0.9 mole percent) tributyltin acetate in cyclohexane. The thus obtained impregnated material was calcined at a temperature of about 538° C. for 6 hours.

Catalyst D (Invention)

A 2 gram quantity of Catalyst A was impregnated, by incipient wetness, with an aqueous solution containing 5 weight percent (1.1 mole percent) phosphoric acid. The thus obtained impregnated material was calcined at a temperature of about 538° C. for 6 hours.

Catalyst E (Invention)

A 2 gram quantity of Catalyst A was impregnated, by incipient wetness, with an aqueous solution containing 10 weight percent (2.2 mole percent) phosphoric acid. The thus obtained impregnated material was calcined at a temperature of about 538° C. for 6 hours.

Catalyst F (Invention)

A 2 gram quantity of Catalyst A was impregnated, by incipient wetness, with an aqueous solution containing 20 weight percent (4.4 mole percent) phosphoric acid. The thus obtained impregnated material was calcined at a temperature of about 538° C. for 6 hours.

EXAMPLE 2

This example illustrates the use of the catalysts described in Example 1 in the conversion of methanol to olefins and/or DME.

In Run 1, a 1.64 gram quantity of Catalyst A described in Example 1 was placed into a stainless steel tube reactor (length: about 18 inches; inner diameter: about 0.5 inch). The steel reactor tube was heated to about 450° C. The reactor pressure was about 0 psig. A methanol/water feed, comprising 20 mole % methanol and 80 mole % water, was introduced to the reactor tube at a flow rate of 25 mL/hour to yield a methanol WHSV of about 4.3 hour$^{-1}$. The product was analyzed by means of a gas chromatograph. Test data results obtained after about 7.0 hours on stream are summarized in the Table.

In Run 2, a 2.03 gram quantity of Catalyst B described in Example 1 was placed into a stainless steel tube reactor (length: about 18 inches; inner diameter: about 0.5 inch). The steel reactor tube was heated to about 456° C. The reactor pressure was about 0 psig. A methanol/water feed, comprising 20 mole % methanol and 80 mole % water, was introduced to the reactor tube at a flow rate of 25 mL/hour to yield a methanol WHSV of about 3.5 hour$^{-1}$. The product was analyzed by means of a gas chromatograph. Test data results obtained after about 6.3 hours on stream are summarized in the Table.

In Run 3, a 2 gram quantity of Catalyst C described in Example 1 was placed into a stainless steel tube reactor (length: about 18 inches; inner diameter: about 0.5 inch). The steel reactor tube was heated to about 450° C. The reactor pressure was about 0 psig. A methanol/water feed, comprising 20 mole % methanol and 80 mole % water, was introduced to the reactor tube at a flow rate of 25 mL/hour to yield a methanol WHSV of about 3.6 hour$^{-1}$. The product was analyzed by means of a gas chromatograph. Test data results obtained after about 7.2 hours on stream are summarized in the Table.

In Run 4, a 2.02 gram quantity of Catalyst D described in Example 1 was placed into a stainless steel tube reactor (length: about 18 inches; inner diameter: about 0.5 inch). The steel reactor tube was heated to about 452° C. The reactor pressure was about 0 psig. A methanol/water feed, comprising 20 mole % methanol and 80 mole % water, was introduced to the reactor tube at a flow rate of 25 mL/hour to yield a methanol WHSV of about 3.5 hour$^{-1}$. The product was analyzed by means of a gas chromatograph. Test data results obtained after about 7.1 hours on stream are summarized in the Table.

In Run 5, a 2.05 gram quantity of Catalyst E described in Example 1 was placed into a stainless steel tube reactor (length: about 18 inches; inner diameter: about 0.5 inch). The steel reactor tube was heated to about 450° C. The reactor pressure was about 0 psig. A methanol/water feed, comprising 20 mole % methanol and 80 mole % water, introduced to the reactor tube at a flow rate of 25 mL/hour to yield a methanol WHSV of about 3.5 hour$^{-1}$. The product was analyzed by means of a gas chromatograph. Test data results obtained after about 7.3 hours on stream are summarized in the Table.

In Run 6, a 2.13 gram quantity of Catalyst F described in Example 1 was placed into a stainless steel tube reactor (length: about 18 inches; inner diameter: about 0.5 inch). The steel reactor tube was heated to about 449° C. The reactor pressure was about 0 psig. A methanol/water feed, comprising 20 mole % methanol and 80 mole % water, was introduced to the reactor tube at a flow rate of 25 mL/hour to yield a methanol WHSV of about 3.3 hour$^{-1}$. The product was analyzed by means of a gas chromatograph. Test data results obtained after about 7.6 hours on stream are summarized in the Table.

TABLE

| Run | Catalyst | Methanol Conversion Wt. % | $\Sigma C_2^=$–$C_4^=$ Selectivity[1] % | DME Selectivity[2] % | Coke[3] Wt. %/ hour |
|---|---|---|---|---|---|
| 1 | A (control) | 92.2 | 80.4 | 13.2 | 2.8 |
| 2 | B (invention) | 86.2 | 90.0 | 5.2 | 1.5 |
| 3 | C (invention) | 87.0 | 84.3 | 11.3 | 1.2 |
| 4 | D (invention) | 86.7 | 90.2 | — | 1.3 |
| 5 | E (invention) | 77.4 | — | 100 | 0.4 |
| 6 | F (invention) | 95.3 | — | 100 | 0.2 |

DME - dimethyl ether
[1]DME Selectivity is defined as the weight % of DME in the product divided by the weight % methanol conversion, multiplied by 100.
[2]$\Sigma C_2^=$–$C_4^=$ Selectivity is defined as the weight % of $\Sigma C_2^=$–$C_4^=$ in the product divided by the weight % methanol conversion, multiplied by 100.
[3]Coke was determined at the end of the reaction by removing the catalysts from the reactor and measuring the coke with a thermal gravimetric analyzer (TGA), manufactured by TA Instruments, New Castle, Delaware.

The test data presented in the Table show that use of inventive Catalysts B, C and D in Runs 2, 3 and 4, respectively, resulted in an increased $C_2$= to $C_4$= selectivity and a considerable decrease in coke production as compared to the use of control Catalyst A in Run 1.

Inventive Run 2 demonstrated a 12 percent increase in $C_2$= to $C_4$= selectivity and a 46 percent decrease in coke production over control Run 1.

Inventive Run 3 demonstrated a 4.9 percent increase in $C_2$= to $C_4$= selectivity and a 57 percent decrease in coke production over control Run 1.

Inventive Run 4 demonstrated a 12 percent increase in $C_2$= to $C_4$= selectivity and a 54 percent decrease in coke production over control Run 1.

The test data presented in the Table also show that use of inventive Catalysts E and F in Runs 5 and 6, respectively, resulted in an increased DME selectivity and a considerable decrease in coke production as compared to the use of control Catalyst A in Run 1.

Inventive Run 5 demonstrated a 658 percent increase in DME selectivity and an 86 percent decrease in coke production over control Run 1.

Inventive Run 6 demonstrated a 658 percent increase in DME selectivity, a 3.4 percent increase in methanol conversion and a 93 percent decrease in coke production over control Run 1.

From the data in the Table, it is readily apparent that the inventive catalyst systems result in decreased coke production and increased olefin yield or increased ether yield, depending on the catalyst system used, when used in the conversion of oxygenated hydrocarbons, as compared to control Catalyst A.

Reasonable variations, modifications, and adaptations can be made within the scope of the disclosure and the appended claims without departing from the scope of this invention.

That which is claimed is:

1. A catalyst system comprising a silicoaluminophosphate impregnated with tributyltin acetate, to thereby form an impregnated silicoaluminophosphate.

2. A catalyst system as recited in claim 1 wherein said impregnated silicoaluminophosphate is calcined to thereby form a calcined impregnated silicoaluminophosphate.

3. A catalyst system as recited in claim 2 wherein said calcining of said impregnated silicoaluminophosphate is conducted at a temperature in the range of from about 200° C. to about 1000° C. for a time period in the range of from about 0.1 hour to about 30 hours.

4. A catalyst system as recited in claim 1 wherein the amount of tributyltin acetate impregnated into said silicoaluminophosphate is in the range upwardly to about 20 weight percent based on the total weight of said impregnated silicoaluminophosphate.

5. A method of preparing a catalyst system comprising the step of impregnating a silicoaluminophosphate with tributyltin acetate, to thereby form an impregnated silicoaluminophosphate.

6. A method in accordance with claim 5 further comprising the step of calcining said impregnated silicoaluminophosphate to thereby form a calcined impregnated silicoaluminophosphate.

7. A method in accordance with claim 6 wherein said step of calcining said impregnated silicoaluminophosphate is conducted at a temperature in the range of from about 200° C. to about 1000° C. for a time period in the range of from about 0.1 hour to about 30 hours.

8. A method in accordance with claim 5 wherein the amount of tributyltin acetate impregnated into said silicoaluminophosphate is in the range upwardly to about 20 weight percent based on the total weight of said impregnated silicoaluminophosphate.

9. A method in accordance with claim 5 wherein said step of impregnating said silicoaluminophosphate comprises mixing, to incipient wetness, said silicoaluminophosphate with a solution comprising said compound.

10. A method in accordance with claim 9 wherein the concentration of tributyltin acetate in said solution is in the range of from about 0.01 mole % to about 10 mole %, based on the total moles of said solution.

11. A catalyst system prepared by the method of claim 5.
12. A catalyst system prepared by the method of claim 6.
13. A catalyst system prepared by the method of claim 7.
14. A catalyst system prepared by the method of claim 8.
15. A catalyst system prepared by the method of claim 9.
16. A catalyst system prepared by the method of claim 10.

17. A process for converting at least a portion of a feedstock comprising methanol to a reaction product comprising at least one compound selected from the group consisting of dimethyl ether, ethylene, propylene, butylene, and mixtures of any two or more thereof, said process comprises contacting said feedstock with the catalyst system of claim 1 at conversion conditions including a temperature in the range of from about 200° C. to about 800° C., a pressure in the range of from about 0 psig to about 500 psig, and a weight hourly space velocity in the range of from about 0.01 hour$^{-1}$ to about 1000 hours$^{-1}$.

18. A process for converting at least a portion of a feedstock comprising methanol to a reaction product comprising dimethyl ether, said process comprises contacting said feedstock with the catalyst system of claim 2 at conversion conditions including a temperature in the range of from about 200° C. to about 800° C., a pressure in the range of from about 0 psig to about 500 psig, and a weight hourly space velocity in the range of from about 0.01 hour$^{-1}$ to about 1000 hours$^{-1}$.

19. A process for converting at least a portion of a feedstock comprising methanol to a reaction product comprising at least one compound selected from the group consisting of dimethyl ether, ethylene, propylene, butylene, and mixtures of any two or more thereof, said process comprises contacting said feedstock with the catalyst system of claim 3 at conversion conditions including a temperature in the range of from about 200° C. to about 800° C., a pressure in the range of from about 0 psig to about 500 psig, and a weight hourly space velocity in the range of from about 0.01 hour$^{-1}$ to about 1000 hours$^{-1}$.

20. A process for converting at least a portion of a feedstock comprising methanol to a reaction product comprising at least one compound selected from the group consisting of dimethyl ether, ethylene, propylene, butylene, and mixtures of any two or more thereof, said process comprises contacting said feedstock with the catalyst system of claim 4 at conversion conditions including a temperature in the range of from about 200° C. to about 800° C., a pressure in the range of from about 0 psig to about 500 psig, and a weight hourly space velocity in the range of from about 0.01 hour$^{-1}$ to about 1000 hours$^{-1}$.

21. A process for converting at least a portion of a feedstock comprising methanol to a reaction product comprising at least one compound selected from the group consisting of dimethyl ether, ethylene, propylene, butylene, and mixtures of any two or more thereof, said process comprises contacting said feedstock with a catalyst system prepared by the method of claim 5 at conversion conditions including a temperature in the range of from about 200° C. to about 800° C., a pressure in the range of from about 0 psig to about 500 psig, and a weight hourly space velocity in the range of from about 0.01 hour$^{-1}$ to about 1000 hours$^{-1}$.

22. A process for converting at least a portion of a feedstock comprising methanol to a reaction product comprising dimethyl ether, said process comprises contacting said feedstock with a catalyst system prepared by the method of claim 6 at conversion conditions including a temperature in the range of from about 200° C. to about 800° C., a pressure in the range of from about 0 psig to about 500 psig, and a weight hourly space velocity in the range of from about 0.01 hour$^{-1}$ to about 1000 hours$^{-1}$.

23. A process for converting at least a portion of a feedstock comprising methanol to a reaction product comprising at least one compound selected from the group consisting of dimethyl ether, ethylene, propylene, butylene, and mixtures of any two or more thereof, said process comprises contacting said feedstock with a catalyst system prepared by the method of claim 7 at conversion conditions including a temperature in the range of from about 200° C. to about 800° C., a pressure in the range of from about 0 psig to about 500 psig, and a weight hourly space velocity in the range of from about 0.01 hour$^{-1}$ to about 1000 hours$^{-1}$.

24. A process for converting at least a portion of a feedstock comprising methanol to a reaction product comprising at least one compound selected from the group consisting of dimethyl ether, ethylene, propylene, butylene, and mixtures of any two or more thereof, said process comprises contacting said feedstock with a catalyst system prepared by the method of claim 8 at conversion conditions including a temperature in the range of from about 200° C. to about 800° C., a pressure in the range of from about 0 psig to about 500 psig, and a weight hourly space velocity in the range of from about 0.01 hour$^{-1}$ to about 1000 hours$^{-1}$.

25. A process for converting at least a portion of a feedstock comprising methanol to a reaction product comprising at least one compound selected from the group consisting of dimethyl ether, ethylene, propylene, butylene, and mixtures of any two or more thereof, said process comprises contacting said feedstock with a catalyst system prepared by the method of claim 9 at conversion conditions including a temperature in the range of from about 200° C. to about 800° C., a pressure in the range of from about 0 psig to about 500 psig, and a weight hourly space velocity in the range of from about 0.01 hour$^{-1}$ to about 1000 hours$^{-1}$.

26. A process for converting at least a portion of a feedstock comprising methanol to a reaction product comprising at least one compound selected from the group consisting of dimethyl ether, ethylene, propylene, butylene, and mixtures of any two or more thereof, said process comprises contacting said feedstock with a catalyst system prepared by the method of claim 10 at conversion conditions including a temperature in the range of from about 200° C. to about 800° C., a pressure in the range of from about 0 psig to about 500 psig, and a weight hourly space velocity in the range of from about 0.01 hour$^{-1}$ to about 1000 hours$^{-1}$.

27. A process for converting at least a portion of a feedstock comprising methanol to at least one ether, said process comprising:

impregnating a silicoaluminophosphate with a solution comprising phosphoric acid, said phosphoric acid present in said solution in the range of from about 10 weight % to about 40 weight %, based on the total weight of said solution, to thereby produce an impregnated silicoaluminophosphate; and contacting said feedstock with said impregnated silicoaluminophosphate at conversion conditions to thereby form a reaction product comprising at least one ether; and recovering said reaction product.

\* \* \* \* \*